United States Patent
Newman et al.

(10) Patent No.: US 11,372,005 B2
(45) Date of Patent: *Jun. 28, 2022

(54) METHOD AND COMPOSITIONS FOR THE TREATMENT AND DETECTION OF ENDOTHELIN-1 RELATED KIDNEY DISEASES

(71) Applicant: MOREHOUSE SCHOOL OF MEDICINE, Atlanta, GA (US)

(72) Inventors: Gale W. Newman, Duluth, GA (US); James W. Lillard, Jr., Smyrna, GA (US); Chamberlain Obialo, Atlanta, GA (US)

(73) Assignee: Morehouse School of Medicine, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/094,175

(22) Filed: Nov. 10, 2020

(65) Prior Publication Data

US 2021/0072261 A1  Mar. 11, 2021

Related U.S. Application Data

(63) Continuation of application No. 13/906,074, filed on May 30, 2013, now Pat. No. 10,866,249, which is a continuation of application No. 13/162,010, filed on Jun. 16, 2011, now Pat. No. 9,255,931.

(60) Provisional application No. 61/344,289, filed on Jun. 24, 2010.

(51) Int. Cl.
| | |
|---|---|
| *A61K 9/19* | (2006.01) |
| *G01N 33/68* | (2006.01) |
| *A61K 38/12* | (2006.01) |
| *G01N 33/74* | (2006.01) |
| *A61K 31/4025* | (2006.01) |
| *A61K 45/06* | (2006.01) |
| *A61K 9/00* | (2006.01) |
| *A61K 31/40* | (2006.01) |
| *A61K 31/422* | (2006.01) |
| *A61K 31/505* | (2006.01) |
| *A61K 31/506* | (2006.01) |
| *C12Q 1/6883* | (2018.01) |
| *G01N 33/569* | (2006.01) |
| *G01N 33/78* | (2006.01) |

(52) U.S. Cl.
CPC ....... *G01N 33/6893* (2013.01); *A61K 9/0019* (2013.01); *A61K 31/40* (2013.01); *A61K 31/4025* (2013.01); *A61K 31/422* (2013.01); *A61K 31/505* (2013.01); *A61K 31/506* (2013.01); *A61K 38/12* (2013.01); *A61K 45/06* (2013.01); *C12Q 1/6883* (2013.01); *G01N 33/56988* (2013.01); *G01N 33/74* (2013.01); *G01N 33/78* (2013.01); *C12Q 2600/106* (2013.01); *C12Q 2600/156* (2013.01); *C12Q 2600/158* (2013.01); *G01N 2333/5754* (2013.01); *G01N 2800/28* (2013.01); *G01N 2800/347* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 10,866,249 B2* | 12/2020 | Newman | G01N 33/56988 |
| 2002/0062121 A1 | 5/2002 | Tryggvason et al. | |
| 2003/0229906 A1 | 12/2003 | Gelman et al. | |
| 2007/0224280 A1 | 9/2007 | Lillard et al. | |
| 2009/0054473 A1 | 2/2009 | Roden et al. | |
| 2009/0238795 A1 | 9/2009 | Sehgal et al. | |
| 2010/0022568 A1 | 1/2010 | Clozel et al. | |
| 2010/0029560 A1 | 2/2010 | Donald | |
| 2010/0204163 A1 | 8/2010 | Melvin, Jr. et al. | |
| 2012/0083421 A1 | 4/2012 | Barasch et al. | |
| 2013/0252898 A1 | 9/2013 | Newman et al. | |

OTHER PUBLICATIONS

Morrow, A., "An overview of Chronic Kidney Disease", Verywellhealth, 2008, pp. 1-6.
Schwimmer, J.—A List of Kidney Diseases, pp. 4-16.
Wyatt, C. M. et al., "The spectrum of kidney disease in patients with AIDS in the era of antiretroviral therapy", Kidney International, 2009, Vo. 7 5, pp. 428-434.
Berliner, A. R. et al., "Observations on a Cohort of HIV-Infected Patients Undergoing Native Renal Biopsy", American Journal of Nephrology, 2008, vol. 28, pp. 478-486.
Zhong, J. et al., "A perspective on chronic kidney disease progression", American Journal of Physiology—Renal Physiology, 2017, vol. 312(3), pp. F375-F384.
Gajjala, P. R. et al., "Cellular and molecular mechanisms of chronic kidney disease with diabetes mellitus and cardiovascular diseases as its comorbidities", Frontiers in Immunology, 2015, vol. 6(340), pp. 1-15.
Chang et al. Plasma Endothelin Levels and Surgically Correctable Pulmonary Hypertension. Ann Thorac Surg 1993;55:450-8 (https://www.annalsthoracicsurgcry.org/articlc/0003-4975(93)91018-1/pdf).
Dhaun et al. (The Endothelin System and Its Antagonism in Chronic Kidney Disease. JASN Apr. 2006, 17 (4) 943-955; DOI: https://doi.org/10.1681/ASN .2005121256. https://jasn.asnjournals.org/content/17/4/943#ref-73.

(Continued)

*Primary Examiner* — Maury A Audet
(74) *Attorney, Agent, or Firm* — Ping Wang; Rimon Law

(57) ABSTRACT

The present application relates to methods of treating HIV-associated nephropathy (HIVAN) and/or focal segmental glomerulosclerosis (FSGS) using endothelin-1 (ET-1) antagonists. The application further relates to a composition for the treatment of HIVAN and/or FSGS. A kit for detecting the presence of ET-1 or ET-1-associated biomarker in a biological sample is also disclosed.

11 Claims, 5 Drawing Sheets

Specification includes a Sequence Listing.

(56) References Cited

OTHER PUBLICATIONS

Kopp et al., "The role of Endothelin-1 [ET-1] in the Pathogenesis of HIV-associated Nephropathy[HIVAN]", Journal of American Society of Nephrology, vol. 19,'pp. 670A, SA-P02496, (abstract only).
Vatter et al. Ambrisentan, a Non-peptide Endothelin Receptor Antagonist. Cardiovascular Drug Reviews, vol. 24, No. 1, pp. 63-76, 2006. https://onlinelibrary.wiley.com/doi/epdf/10.1111/j.1527-3466.2006.00063 x.
Ohkita et al. Drug discovery for overcoming chronic kidney disease (CKD): the endothelin ET B receptor/nitric oxide system functions as a protective factor in CKD. J Pharmacol Sci. Jan. 2009;109(1):7-13. https://www.jstage.jst.go.jp/article/jphs/109/1/109_08R 1 OFM/_pdf/-char/en.
Dschietzig et al. Relaxin, a pregnancy hormone, is a functional endothelin-1 antagonist: attenuation of endothelin-1-mediated vasoconstriction by stimulation of endothelin type-B receptor expression via ERK-1/2 and nuclear factor-kappaB. Gire Res. Jan. 10, 2003; 92(1 ):32-40.
Chen, H., et al., "Plasma and urinary endothelin-1 in focal segmental glomerulosclerosis", Journal of Clinical Laboratory Analysis, vol. 15, pp. 59-63, (2001 ).
Barton, M., "Reversal of proteinuric renal disease and the emerging role of endothelin", Nature Clinical Practice Nephrology, vol. 4, No. 9, pp. 490-501, (2008).
Izzedine, H., et al., "Antiviral Drug-Induced Nephrotoxicity", Am. J. Kidney Dis., vol. 45, pp. 804-817, (2005).
Schwartz, E.J., et al., "Highly Active Antiretroviral Therapy and the Epidemic of HIV+ End-Stage Renal Disease", JASN, vol. 16, pp. 2412-2420, (2005).
Szczech, L.A., et al., "The clinical epidemiology and course of the spectrum of renal diseases associated with HIV Infection", Kidney Int., vol. 66, pp. 1145-1152, (2004).
Yahaya, I., et al., "Interventions for HIV-associated nephropathy", Cochrane Database of Systematic Reviews, (2009).
Kirkby, N.S., et al., "The endothelin system as a therapeutic target in cardiovascular disease: great expectations or bleak house?", British Journal of Pharmacology, vol. 153, pp. 1105-1119, (2008).
Sorokin, A., et al., "Physiology and pathology of endothelin-1 in renal mesangium", Am J Physiol Renal Physiol, vol. 285, pp. F579-F589, (2003).
Ebihara, I., et al., "Increased endothelin-1 mRNA expression in peripheral blood monocytes of dialysis patients", Peritoneal Dialysis International, vol. 17, pp. 595-601, (1997).
Bodi, I., et al., "Macrophages in human immunodeficiency virus-associated kidney diseases", American Journal of Kidney Diseases, vol. 24, pp. 762-767, (1994).
Treiber, F.A., et al., "Racial Differences in Endothelin-1 at Rest and in Response to Acute Stress in Adolescent Males", Hypertension, vol. 35, pp. 722-725, (2000).
Treiber, F.A., et al., "Plasma Endothelin-1 Release During Acute Stress: Role of Ethnicity and Sex", Psychosom Med., vol. 64, pp. 707-713, (2002).
Winston J., et al., "HIV-associated nephropathy", Mt. Sinai J. Med., vol. 65, pp. 27-32, (1998).
Rybicki, A.C., et al., "Increased Levels of Endothelin-1 in Plasma of Sickle Cell Anemia Patients", Blood, vol. 92, pp. 2594-2596 (1998).
Graido-Gonzalez, E., et al., "Plasma Endothelin-1, Cytokine, and Prostaglandin E2Levels in Sickle Cell Disease and Acute Vasa-Occlusive Sickle Crisis", Blood, vol. 92, pp. 2551-2555, (1998).
Boone, C.A., "End-Stage Renal Disease in African-Americans", Nephrology Nursing Journal, vol. 27, pp. 597-600, (2000).
Kao, L., et al., "A genome-wide admixture scan identifies MYH9 as a candidate locus associated with non-diabetic end stage renal disease in African Americans", Nature Genetics, vol. 40, pp. 1185-1192, (2008).
Singh, N., et al., "CKD in MYH9-Related Disorders", American Journal of Kidney Diseases, vol. 54, pp. 732-740, (2009).
Dhaun, N., et al., "Selective Endothelin—A Receptor Antagonism Reduces Proteinuria, Blood Pressure, and Arterial Stiffness in Chronic Proteinuric Kidney Disease", Hypertension, vol. 57, p. 772-779, (2011).
File history of U.S. Appl. No. 13/906,074, filed May 30, 2013.
File history of U.S. Appl. No. 13/162,010, filed Jun. 16, 2011.

\* cited by examiner

SEQUENCE LISTING

<160> NUMBER OF SEQ ID NOS: 8

<210> SEQ ID NO 1
<211> LENGTH: 21
<212> TYPE: DNA
<213> ORGANISM: artificial
<220> FEATURE:
<223> OTHER INFORMATION: ppET-1 forward primer

<400> SEQUENCE: 1
tggacatcat ttgggtcaac a                                        21

<210> SEQ ID NO 2
<211> LENGTH: 19
<212> TYPE: DNA
<213> ORGANISM: artificial
<220> FEATURE:
<223> OTHER INFORMATION: ppET-1 reverse primer

<400> SEQUENCE: 2
tctcttggac ctaggcttc                                           19

<210> SEQ ID NO 3
<211> LENGTH: 18
<212> TYPE: DNA
<213> ORGANISM: artificial
<220> FEATURE:
<223> OTHER INFORMATION: ECE-1 forward primer

<400> SEQUENCE: 3
aaccttcgcc gaggacag                                            18

<210> SEQ ID NO 4
<211> LENGTH: 18
<212> TYPE: DNA
<213> ORGANISM: artificial
<220> FEATURE:
<223> OTHER INFORMATION: ECE-1 reverse primer

<400> SEQUENCE: 4

```
ggctgatttt cgggtttc                                                    18

<210> SEQ ID NO 5
<211> LENGTH: 20
<212> TYPE: DNA
<213> ORGANISM: artificial
<220> FEATURE:
<223> OTHER INFORMATION: 18s rRNA forward primer

<400> SEQUENCE: 5
gtaacccgtt gaaccccatt                                                  20

<210> SEQ ID NO 6
<211> LENGTH: 20
<212> TYPE: DNA
<213> ORGANISM: artificial
<220> FEATURE:
<223> OTHER INFORMATION: 18s rRNA reverse primer

<400> SEQUENCE: 6
ccatccaatc ggtagtagcg                                                  20

<210> SEQ ID NO 7
<211> LENGTH: 23
<212> TYPE: DNA
<213> ORGANISM: artificial
<220> FEATURE:
<223> OTHER INFORMATION: Lys198Asn forward primer

<400> SEQUENCE: 7
gtcggagacc atgagaaaca gcg                                              23

<210> SEQ ID NO 8
<211> LENGTH: 23
<212> TYPE: DNA
<213> ORGANISM: artificial
<220> FEATURE:
<223> OTHER INFORMATION: Lys198Asn reverse primer

<400> SEQUENCE: 8
gttttgaacg aggacgctgg tcc                                              23
```

METHOD AND COMPOSITIONS FOR THE TREATMENT AND DETECTION OF ENDOTHELIN-1 RELATED KIDNEY DISEASES

This application is a Continuation of U.S. application Ser. No. 13/906,074, filed May 30, 2013, which is a Continuation of U.S. application Ser. No. 13/162,010, filed Jun. 16, 2011, now U.S. Pat. No. 9,255,931, which claims priority from Provisional Application No. 61/344,289, filed on Jun. 24, 2010. The entirety of the aforementioned applications is incorporated herein by reference.

This application was made with U.S. Government support under Grant No. 5P20RR011104, awarded by the NIH/NCDD/Clinical Research Centers. Thus, the U.S. Government may have certain rights in this application.

FIELD

This application relates generally to medical treatment and detection and, in particular, to the treatment and detection of endothelin-1 (ET-1) related nephropathy, such as focal segmental glomerulosclerosis (FSGS) and HIV-associated nephropathy (HIVAN).

BACKGROUND

HIV associated nephropathy (HIVAN) affects predominantly African Americans with HIV-1 infection, and is the most common cause of renal failure in HIV positive patients. The pathological features of HIVAN include collapsing focal segmental glomerulosclerosis (FSGS) with microcystic tubular dilation and interstitial inflammation. Highly active antiretroviral therapy (HAART) appears to limit the progression to end-stage renal disease (ESRD), but is not successful in all cases (Schwartz et al., *J. Am. Soc. Nephrol.* 16:2412-2420, 2005), and long term use of antiretrovirals can be toxic to the kidneys (Izzedine et al., *Am. J. Kidney Dis.* 45:804-817, 2005). Untreated HIV positive individuals who develop HIVAN can progress rapidly to ESRD within 6-12 months (Szczech et al., *Kidney Int* 66:1145-1152, 2004).

There is no standard treatment of HIVAN and randomized controlled clinical trials have not been performed (Yahaya et al., Cochrane Database of Systematic Reviews, 2009). Most treatment regimens have been based on therapies used to treat the symptoms of kidney disease. These drugs have included angiotensin converting enzyme inhibitors, steroids and cyclosporine; however, conclusive data concerning their efficacy is not available (Yahaya et al. supra). There exists a need to discover more effective pharmacological agents to treat HIVAN and reduce the progression to ESRD.

There exists a need for more effective pharmacological agents for treating HIVAN and other kidney diseases, and for identifying patients benefiting from such treatment. Accordingly, the present application provides such compositions and methods for use.

SUMMARY

One aspect of the present invention relates to a method of treating HIV-associated nephropathy and/or focal segmental glomerulosclerosis in a subject by administering to said subject an effective amount of an ET-1 antagonist, wherein said subject has increased amount of circulating plasma ET-1 compared to other HIV positive patients and healthy controls.

Another aspect of the present invention relates to a method for monitoring the effectiveness of a treatment for HIV-associated nephropathy (HIVAN) and/or focal segmental glomerulosclerosis (FSGS) in a subject. In one embodiment, the method comprises the steps of: (a) performing a first measurement of ET-1 and/or an ET-1-associated biomarker in a first biological sample from the subject, (b) performing a second measurement of ET-1 and/or an ET-1-associated biomarker in second biological sample from the subject, and (c) determining an efficacy of the treatment based on the results of (a) and (b). In a related embodiment, step (a) is performed prior to the initiation of the treatment and step (b) is performed after the initiation of the treatment.

Another aspect of the present invention relates to a method for diagnosis of HIVAN and/or FSGS in a subject. The method comprises the steps of comparing a level of an ET-1-associated biomarker in a biological sample obtained from the subject to a threshold level; and making a diagnosis based on a result from the comparing step. In a related embodiment, the method further comprises the step of determining the level of the ET-1-associated biomarker in the biological sample obtained from the subject.

Another aspect of the present invention relates to a composition for the treatment of HIV-associated nephropathy and/or focal segmental glomerulosclerosis. In one embodiment, the composition comprises an ET-1 antagonist and a pharmaceutically acceptable carrier.

Another aspect of the present invention relates to a kit for detecting the presence of ET-1 or ET-1 associated biomarker in a biological sample.

DETAILED DESCRIPTION

Figure 1:
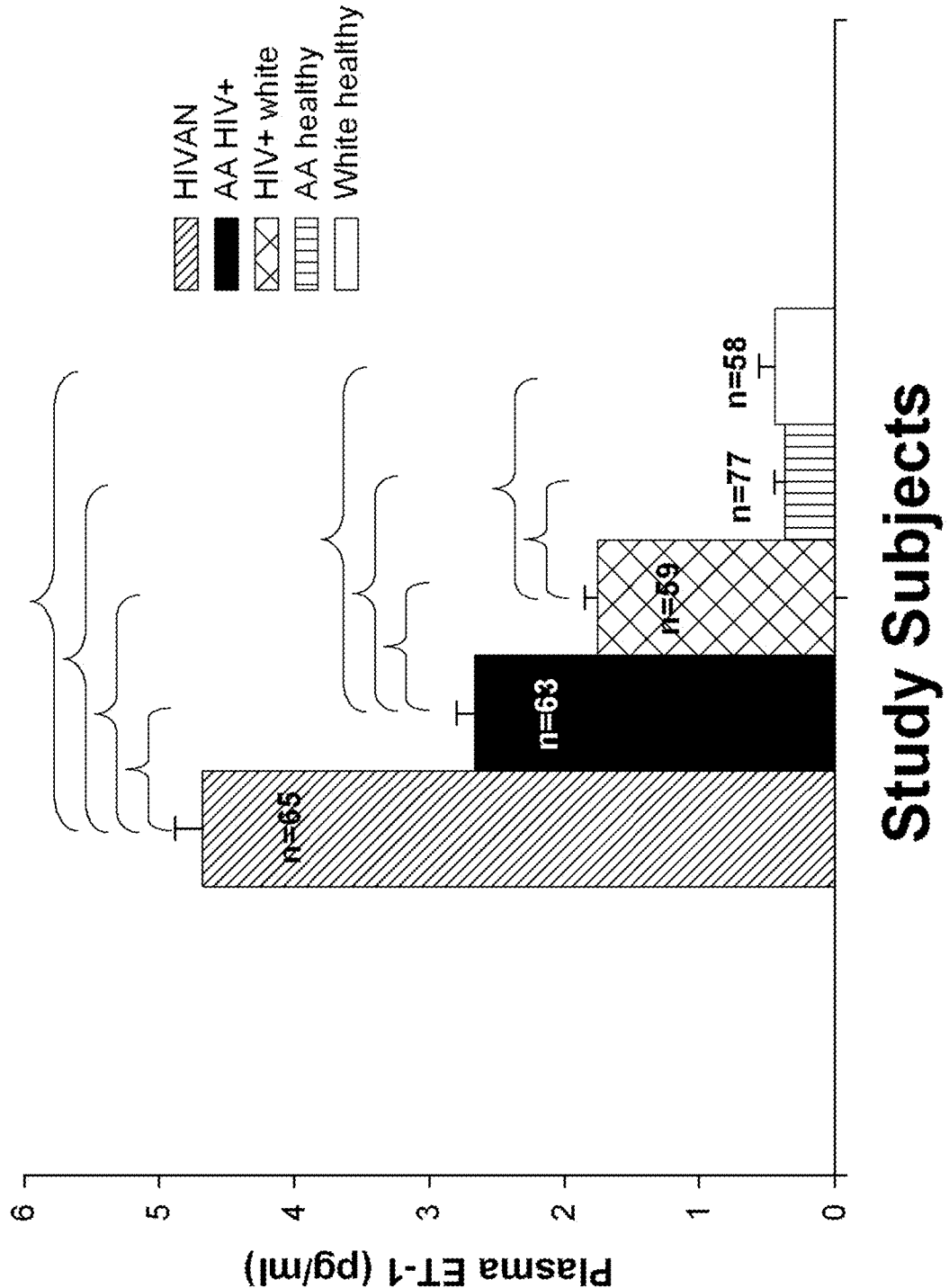
FIG. 1 is a diagram showing that ET-1 plasma concentrations in healthy controls and HIV infected patients.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention.

In case of conflict, the present specification, including definitions, will control. Following long-standing patent law convention, the terms "a", "an" and "the" mean "one or more" when used in this application, including in the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter. As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

The term "direct ET-1-associated biomarker" as used herein, refers to proteins and/or polynucleotides directly linked to ET-1 expression or ET-1 activity. Exemplary ET-1-associated biomarkers include, but are not limited to proteins, nucleic acids, antibodies, single nucleotide polymorphisms (SNPs) and/or probes therefrom capable of specifically detecting the presence or expression (e.g., in a biological sample from a subject) of preproendothelin (ppET-1), proendothelin-1 (pET-1), big ET-1, ET-1, and derivatives therefrom.

The term "indirect ET-1-associated biomarker" as used herein, refers to proteins and/or polynucleotides indirectly correlated with ET-1 expression or ET-1 activity. Exemplary ET-1-associated biomarkers include, but are not limited to endothelin converting enzyme (ECE), cystatin C; creatinine, including albumin-creatinine ratio (ACR); and other measures characteristic of kidney diseases The term "ET-1-associated biomarker" as used herein, refers to both direct ET-1-associated biomarker and indirect ET-1-associated biomarker.

The term "ET-1 level" refers to an expression level corresponding to any one of the direct ET-1-associated biomarkers, included, but not limited to preproendothelin (ppET-1), proendothelin-1 (pET-1), big ET-1, ET-1, and derivatives therefrom.

Nephropathy including but not limit to, glomerulopathy, glomerulitis, glomerulonephritis, glomerulonephrosis, tubulitis. HIVAN, FSGS, drug induced nephropathy, nephron loss, hyperfiltration, chronic pyelonephritis, Type I RPG/Type II hypersensitivity, Goodpasture's syndrome, Type II RPG/Type III hypersensitivity, Lupus (DPN), IgA/Berger's nephropathy, Wegener's granulomatosis, Microscopic polyangiitis, RTA (RTA 2), Fanconi syndrome, Bartter syndrome, Gitelman syndrome, Liddle's syndrome RTA (RTA 1), diabetes insipidus (Nephrogenic), renal papilla, renal papillary necrosis, major calyx/pelvis, hydronephrosis, pyonephrosis, reflux nephropathy, acute tubular necrosis, interstitial nephritis, pyelonephritis, danubian endemic, familial nephropathy, renal failure, acute renal failure, chronic renal failure, uremic pericarditis, uremia, renal artery stenosis, renal Ischemia, hypertensive nephropathy, renovascular hypertension, analgesic nephropathy, renal osteodystrophy, nephroptosis, and Abderhalden-Kaufmann-Lignac syndrome.

The term "control subject" refers to a comparative subject providing a means for determining whether treatment with an ET-1 antagonist is warranted, for determining the effectiveness of a given treatment, or for determining whether a given subject is at risk for developing a disease characterized by increased ET-1 levels as further discussed herein. A "control subject" can refer to a healthy or diseased subject receiving a mock treatment (e.g., saline alone), a healthy subject receiving the same treatment as a diseased patient or subject under assessment for disease risk, a diseased subject known to exhibit increased ET-1 levels, or combination thereof. Additionally, a healthy or diseased subject may be of the same or different ethnicity as the subject under assessment for disease risk and/or treatment.

Endothelin-1 (ET-1) is the most potent vasoconstrictor known. It is synthesized by many cell types, including vascular endothelial cells, glomerular mesangial cells, renal epithelial cells, neutrophils, monocytes and macrophages. ET-1 is generated from precursor peptides via a two-step proteolytic pathway. Transcription of a gene on chromosome 6 generates an mRNA encoding the 212-amino acid peptide pre-proendoethelin-1 (preproET-1 or ppET-1), which once translated, is stripped of its signal sequence and secreted into the cytoplasm as proET-1 (Kirby et al., Br. J. Pharmacol., 153:1105-1119, 2008). ProET-1 is further cleaved by a furin-like endopeptidase to a biologically inactive 38-amino acid precursor, "big ET-1", which circulates in plasma at low concentration. Removal of a further 17 COOH-terminal residues, classically but not exclusively by a membrane-bound metalloproteinase, ET-converting enzyme (ECE), results in formation of the mature, biologically active 21-amino acid pET-1 peptide, the most potent vasoconstrictor known.

ET-1 binds to $ET-1_A$ and $ET-1_B$ receptors. In the kidney, ET-1 causes diminished blood flow and glomerular filtration rate. ET-1 is elevated in many renal diseases. ET-1 induces vasoconstriction, cell proliferation and extracellular matrix formation, all features of chronic renal disease. Mesangial cells possess receptors for ET-1 and can also produce ET-1, which in turn stimulates mesangial cell proliferation and extracellular matrix hypersecretion (Sorokin, et al., Am. J. Physiol Renal Physiol 285:F579-F589, 2003). Studies have shown increased production of urinary and plasma ET-1 concentrations in patients with idiopathic FSGS and IgA nephropathy (Chen et al., J Clin. Lab Anal. 15:59-63-16, 2001). Both resting and stimulated macrophages produce and release ET-1 (Ebihara et al., Periton. Dialy. Intern. 17:595-601, 1997). Macrophages are a major constituent of the interstitial infiltrate that is frequently found in close proximity to sclerotic glomeruli and plays a role in the development of HIVAN (Bodi et al., Am. J. Kidney Dis. 24:762-767, 1994).

Normotensive and hypertensive African American adults and adolescents produce more ET-1 than their Caucasian counterparts at rest and in response to stress (Treiber et al.,

*Hypertens.* 35:722-725, 2000; Treiber et al., *Psychosomatic Medicine* 64:707-713, 2002). HIVAN affects predominantly African Americans with HIV-1 infection, and is the most common cause of renal failure in AIDS patients (Winston et al., *Mt. Sinai J. Med.* 65:27-32, 1998). Sickle cell anemia, a disease most prevalent in individuals of African descent, also is associated with increased ET-1 levels. Plasma ET-1 is elevated in sickle cell anemia patients as well as those undergoing acute vaso-occlusive sickle crisis when compared to African Americans without sickle cell disease (Rybicki et al., *Blood* 92:2594-2596, 1998; Graido-Gonzalez et al., *Blood* 92:2551-2555, 1998). In addition, African Americans have a higher incidence of chronic kidney disease (Boone, *Nephrol. Nurs. J.* 27:597-600, 2000) that may be related to the MYH9 gene (Kao et al., *Nat. Genet.* 40:1185-1192, 2008); Singh et al., *Am. J Kidney Dis.* 54:732-740, 2009).

Treatment Methods

One aspect of the present invention relates to a method of treating HIV-associated nephropathy (HIVAN) and/or focal segmental glomerulosclerosis (FSGS) comprising administering into a subject an effective amount of an ET-1 antagonist. In a preferred embodiment, the subject exhibits increased levels of ET-1 compared to other HIV positive patients or healthy controls. The method is particularly suited for ethnic groups and/or patients exhibiting higher than normal ET-1 levels, including, but not limited to HIVAN patients, FSGS patients, African American HIV-positive patients, HIV-positive patients, and patients with other kidney diseases, including, but not limited to IgA nephropathy, diabetic nephropathy, Sickle cell nephropathy, and renovascular hypertension.

In one embodiment, the ET-1 antagonist binds to one or more of ET-1, ET-2, ET-3, or a peptide derivative thereof. In another embodiment, the ET-1 antagonist binds to an ET receptor, such as $ET-1_A$. In either case, the ET-1 antagonist preferably prevents or reduces the interaction between ET-1 to an ET receptor. As such, the ET-1 antagonist may be a small molecule, such as an organic compound, or a large molecule, such as a protein, peptide, antibody, soluble ET receptor, nucleic acid, oligonucletide, small interferring RNA (siRNA), and the like.

Exemplary ET-1 antagonists may selected from the group consisting of sitaxentan, ambrisentan, atrasentan, BQ-123, bosentan and tezosentan. ET-1 antagonists are well know to those skilled in the art, and may include any of those disclosed in U.S. Patent Application Publication No. 2010/0022568 to Clozel et al., the disclosure of which is incorporated by reference herein.

An ET-1 antagonist may be administered by any route suitable for reducing ET-1 levels in the subject compared to a control subject, including, but not limited to intravenous, intramuscular, nasal, transdermal, transmucosal, buccal, sublingual, oral, subdermal administration, or combinations thereof.

In certain embodiments, the ET-1 antagonist is infused locally into the kidney. The ET-1 antagonist may be introduced into the kidney by intravenous, intrarterial, or retrograde infusion. In one embodiment, the vis infused through the vene renalis. In another embodiment, the ET-1 antagonist is infused through the superior mesenteric artery. In yet another embodiment, the ET-1 antagonist is infused through a retrograde catheter into the pyelic cavity. Since only a relatively small amount of ET-1 antagonist is needed for the kidney infusion, the antagonist-related toxicity is reduced. In yet another embodiment, the kidney is perfused with the ET-1 antagonist, i.e., the ET-1 antagonist enters the kidney through the vene renalis or the superior mesenteric artery, and is collected through the superior mesenteric artery or vene renalis. Since the leftover ET-1 antagonist does not enter the blood circulation, a large amount of ET-1 antagonist may be used for the perfusion. In addition, a close-circuit perfusion allows constant exposure to virus over an extended period of time (e.g., 10-60 minutes).

The ET-1 antagonist may be administered to a subject exhibiting an ET-1 level or ET-1-associated biomarker level of at least about 5%, 10%, 15%, 20%, 25%, 30%, 35%, 40%, 45%, 50%, 55%, 60%, 65%, 70%, 75%, 80%, 85%, 90%, 95%, or 100% higher than the corresponding level in a control subject. Alternatively, the ET-1 antagonist may be administered to a subject exhibiting an ET-1 level or ET-1-associated biomarker level of at least about at least about 1.5 fold, 2-fold, 2.5-fold, 3-fold, 4-fold, 5-fold, 10-fold, 15-fold, 20-fold, 30-fold, 40-fold, 50-fold, or 100-fold higher than the corresponding level in a control subject. Formulations and routes of administering the ET-1 antagonists in the claimed treatment methods are detailed below.

Determining Effectiveness of a Treatment

In another aspect, the present invention provides a method for monitoring the effectiveness of a treatment for HIVAN, FSGS, or other kidney-related disease in a subject. In one embodiment, the method comprises the steps of (a) performing a first measurement of ET-1 and/or an ET-1-associated biomarker in a first biological sample from the subject, (b) performing a second measurement of ET-1 and/or an ET-1-associated biomarker in second biological sample from the subject, and (c) determining the effectiveness of the treatment based on the results of steps (a) and (b). In a preferred embodiment, step (a) is performed prior to the initiation of the treatment and step (b) is performed after the initiation of the treatment.

The ET-1-associated biomarker may be a direct ET-1-associated biomarker or an indirect ET-1 associated biomarker. In one embodiment, the ET-1-associated biomarker is a direct ET-1-associated biomarker selected from the group consisting of preproendothelin (ppET-1), proendothelin-1 (pET-1), big ET-1, ET-1, and derivatives therefrom. In another embodiment, the ET-1-associated biomarker is an indirect ET-1-associated biomarker selected from the group consisting of endothelin converting enzyme (ECE), cystatin C, creatinine, albumin-creatinine ratio (ACR); and other measures characteristic of kidney diseases. The biological sample may be derived from blood, plasma, urine, saliva or tissue.

An exemplary method for detecting the presence of the ET-1-associated biomarker in a biological sample involves obtaining a biological sample from a test subject and contacting the biological sample with a binding agent capable of binding to and facilitating detection of the ET-1-associated biomarker. The binding reagent may be an antibody, protein, peptide, polynucleotide, oligonucleotide, fragment thereof, or conjugate thereof.

A preferred agent for detecting an ET-1-associated biomarker peptide or protein, such as ET-1, is an antibody or a portion thereof that binds specifically the biomarker. Preferred agents for detecting ET-1-associated mRNAs include oligonucleotide probes capable of hybridizing to an ET-1-associated mRNA in a biological sample or of facilitating reverse transcriptase-based assays for detection of ET-1 associated biomarkers in the biological sample, such as ET-1 mRNA.

Detection of the ET-1-associated biomarker may be facilitated through the use of secondary binding agents and detection schemes well known to those skilled in the art. Assays including but not limited to immunoassay and RT-PCR analyses may be used to quantify the amount of expression or activity of the ET-1-associated biomarker in the biological sample. Such quantification may be useful, for example, to determine the progression or severity of HIVAN, FSGS, or a given kidney disease, or to monitor the effectiveness of a treatment therefore using the ET-1 antagonists of the present invention. Immunoassay and RT-PCR methodologies for use in the present invention include those described in the Examples below and in U.S. Patent Application Publication No. 2010/0029560 to Donald et al., the disclosure of which is incorporated by reference herein.

Diagnosis Method

In another aspect, the present invention provides a method for diagnosis of HIVAN, FSGS, or other kidney diseases in a subject. In one embodiment, the method comprises the steps of comparing a level of an ET-1-associated biomarker in a biological sample obtained from the subject to a threshold level, and making a diagnosis based a result from the comparing step. In one embodiment, the biological sample is a plasma sample and the ET-1-associated biomarker is ET-1. In another embodiment, the threshold level is a plasma ET-1 level at about 4 pg/ml and a test subject is deemed to have a high risk of HIVAN and/or FSGS, if the plasma ET-1 level in the subject is higher than the threshold level. In another embodiment, the threshold level is a plasma ET-1 level at about 4.5 pg/ml and a test subject is deemed to have a high risk of HIVAN and/or FSGS, if the plasma ET-1 level in the subject is higher than the threshold level. In another embodiment, the level of the ET-1-associated biomarker is the ppET-1 mRNA level in peripheral blood derived macrophages that are harvested from the subject and cultured in the presence of HIV Nef. In another embodiment, the level of the ET-1-associated biomarker is the ppET-1 mRNA level in peripheral blood derived macrophages that are harvested from the subject and cultured in the presence of 10 ng/ml HIV Nef for four hours and the threshold value is about 5 copies of ppET-1 mRNA per $10^6$ copies of 18 s rRNA, as determined by reverse transcriptase-real time quantitative PCR. In another embodiment, the method further comprises the step of determining a level of an ET-1-associated biomarker in a biological sample for the subject.

In another embodiment, the ET-1-associated biomarker is selected from the group consisting of preproendothelin (ppET-1), proendothelin-1 (pET-1), BIG ET-1, ET-1, derivatives therefrom, endothelin converting enzyme (ECE), cystatin C, creatinine, albumin-creatinine ratio (ACR) or other measures characteristic of kidney diseases. The biological sample can be blood, plasma, urine, saliva or tissue.

Pharmaceutical Compositions

Another aspect of the present invention relates to a composition for the treatment of HIVAN and/or FSGS. In one embodiment, the composition comprises an ET-1 antagonist and a pharmaceutically acceptable carrier. In one embodiment, the ET-1 antagonist binds to one or more of ET-1, ET-2, ET-3, or a peptide derivative thereof. In another embodiment, the ET-1 antagonist binds to an ET receptor, such as ET-$1_A$. In either case, the ET-1 antagonist preferably prevents or reduces the interaction between ET-1 to an ET receptor. As such, the ET-1 antagonist may be a small molecule, such as an organic compound, or a large molecule, such as a protein, peptide, antibody, soluble ET receptor, nucleic acid, oligonucletide, small interfering RNA (siRNA), and the like.

Exemplary ET-1 antagonists may selected from the group consisting of sitaxentan, ambrisentan, atrasentan, BQ-123, bosentan and tezosentan. ET-1 antagonists are well know to those skilled in the art, and may include any of those disclosed in U.S. Patent Application Publication No. 2010/0022568 to Clozel et al., the disclosure of which is incorporated by reference herein.

A pharmaceutical composition in accordance with the present invention includes a pharmaceutically acceptable carrier. As used herein, a "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. See e.g., A. H. Kibbe Handbook of Pharmaceutical Excipients, 3rd ed. Pharmaceutical Press, London, UK (2000). Except insofar as any conventional media or agent is incompatible with the active agent(s), use thereof in the compositions is contemplated. Supplementary agents can also be incorporated into the compositions.

In addition, the pharmaceutical composition may additionally include other bioactive agents, such as angiotensin-converting enzyme (ACE) inhibitors, used in conjunction with the ET-1 antagonists of the present invention. Examples of ACE inhibitors include, but are not limited to, sulfhydryl-containing agents such as captopril and zofenopril; dicarboxylate-containing agents, such as enalapril, ramipril, quinapril, perindopril, lisinopril, benazepril, imidapril, zofenopril; and phosphonate-containing agents, such as fosinopril.

A pharmaceutical composition of the invention may be formulated for compatibility with any route of administration suitable for reducing ET-1 levels or ET-1 activity in a patient. Exemplary routes of administration include intravenous, intramuscular, nasal, transdermal, transmucosal, buccal, sublingual, oral, subdermal, or combination thereof. Solutions or suspensions used for such formulations may include any of the following components, including a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The pharmaceutical composition can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™

(BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active ET-1 antagonist and/or other additional bioactive agents in a pharmaceutically effective amount in an appropriate solvent with one or a combination of ingredients enumerated above, as required, followed by filtered sterilization. Generally, dispersions are prepared by incorporating the active agent(s) into a sterile vehicle which contains a basic dispersion medium and the required other ingredients from those enumerated above. In the case of sterile powders for the preparation of sterile injectable solutions, the preferred methods of preparation are vacuum drying and freeze-drying, which can yield a powder of the active, ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active agent(s) can be incorporated with excipients and used in the form of tablets, troches, or capsules. Oral compositions can also be prepared using a fluid carrier for use as a mouthwash, wherein the active agent(s) in the fluid carrier are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the active agent(s) may be delivered in the form of an aerosol spray from pressured container or dispenser which contains a suitable propellant, e.g., a gas such as carbon dioxide, or a nebulizer.

Systemic administration can also be by transmucosal, buccal, or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the bioactive agent(s) may be formulated into ointments, salves, gels, or creams as generally known in the art.

The ET-1 antagonists can also be prepared in the form of suppositories (e.g., with conventional suppository bases such as cocoa butter and other glycerides) or retention enemas for rectal delivery.

The ET-1 antagonist formulations may be prepared using carriers protecting the ET-1 antagonist against rapid elimination from the body, such as a controlled release formulations, including implants, nanoparticles, microparticles, and microencapsulated delivery systems. Controlled release nanoparticles are described in U.S. Patent Application Publication No. 2007/0224280 to Lillard et al., the disclosure of which is incorporated by reference herein. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal formulations (including liposomes targeted to infected cells with monoclonal antibodies to viral antigens) can also be used as pharmaceutically acceptable carriers. Liposomal formulations can be prepared according to methods well known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active agent(s) calculated to produce the desired therapeutic effect in association with the required pharmaceutical carrier. The specification for the dosage unit forms of the invention are dictated by and directly dependent on the unique characteristics of the active agent(s) and the particular therapeutic effect to be achieved, and the limitations inherent in the art of formulating such active agent(s) for the treatment of individuals.

Toxicity and therapeutic efficacy of the active agent(s) of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Active agents exhibiting large therapeutic indices are preferred. While active agents exhibiting toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of the active agents lies preferably within a range of circulating concentrations that include the ED50 with little or no toxicity. The dosage may vary within this range depending upon the dosage form employed and the route of administration utilized. For any active agents used in the method of the invention, the therapeutically effective dose can be estimated initially from cell culture assays. A dose may be formulated in animal models to achieve a circulating plasma concentration range that includes the IC50 (i.e., the concentration of the test agent which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a kit, container, pack, or dispenser, together with instructions for administration.

Kits

The invention also encompasses kits for detecting the presence of an ET-1-associated biomarkers in a biological sample, the kit comprising reagents for measuring an ET-1-associated biomarker in a biological sample. Preferably, the reagents include at least one binding agent in the form of a binding agent capable of binding to and facilitating detection of the ET-1-associated biomarker. The binding agent may be an antibody, protein, peptide, polynucleotide, oligonucleotide, fragment thereof, or conjugate thereof.

A preferred binding agent for detecting an ET-1-associated biomarker peptide or protein, such as ET-1, is an antibody or a portion thereof that binds specifically the biomarker. Preferred binding agents for detecting ET-1-associated mRNAs include oligonucleotide probes capable of hybridizing to an ET-1-associated mRNA in a biological sample or of facilitating reverse transcriptase-based assays for detection of ET-1 associated biomarkers in the biological sample, such as ET-1 mRNA (as further described below).

Binding agents for detection of ET-1 associated biomarkers may be prepared by methods known in the art. The kit may contain means for determining the amount of the ET-1 associated biomarker protein or mRNA in the sample; and means for comparing the amount of ET-1-associated biomarker in the sample with a control or standard. The binding agent can be packaged in a suitable container.

The kit may further include a label or packaging insert including a description of the components or instructions for use. Exemplary instructions may include, for example, instructions for collecting biological sample(s), for detecting ET-1-associated biomarker(s), and for interpreting the results. The kits described above may additionally include liquids suitable for resuspending any of the kit reagents, along with one or more container(s) for collecting biological sample(s), and/or centrifuge filter(s) for isolating components in the biological sample(s).

The present invention is further illustrated by the following examples which should not be construed as limiting. The contents of all references, patents and published patent applications cited throughout this application, as well as the Figures are incorporated herein by reference.

EXAMPLE 1: DETECTION OF ET-1 AND ET-1-ASSOCIATED MARKERS

Study Subject

Patients with biopsy-proven HIVAN were also recruited from various academic medical centers in the United States. Information on these patients was limited to diagnosis and race. Patient charts were reviewed for HIV and HIVAN status. HIV sero positive patients who presented with proteinuria, >2 g/day, and elevated blood creatinine levels, >2.0 mg/dL, were either biopsied for HIVAN confirmation, or were diagnosed presumptively as having HIVAN after eliminating factors such as hypertension, hepatitis and diabetes. HIV seropositive patients lacking renal disease were enrolled in the study and designated "no history of kidney disease" if: (1) they had no proteinuria (dipstick negative or trace proteinuria <0.15 g/d), (2) their serum creatinine was <2 mg/dL during their previous two clinic visits within a year and at the time of their blood donation; (3) their CD4$^+$ T cells were greater than 200/mm$^3$; and (4) they had no AIDS defining illness. Healthy controls were seronegative for HIV infection, had no history of kidney disease and were not hypertensive.

A total of 239 patients were enrolled in this study: HIVAN (n=64), African American HIV seropositive without kidney disease (n=75), Caucasian HIV seropositive without kidney disease (n=48), and healthy controls (n=134; 75 African American and 59 Caucasian). Human subject samples were collected in accordance with protocols approved by the Institutional Review Board and the Human Subjects Research Committee at all institutions, and informed consent was obtained from all patients and healthy volunteers.

Blood Collection

One 10 ml EDTA tube was used to collect whole blood from patients. The tubes were centrifuged, and plasma was collected and frozen at −80° C. until analysis for ET-1.

ET-1 Quantification

ET-1 levels present in plasma were determined by colorimetric ELISA. ET-1 was extracted from the plasma samples using acetone:1N HCl:water (40:1:5) Cross reactivity for big ET-1 was less than 1%, while ET-2 and ET-3 had a 45% and 14% cross reactivity respectively as determined by the manufacturer. The plates were measured using a microplate reader set at 450 rim. Samples were assayed in triplicate.

Immunohistochemistry

Twelve biopsy samples from 4 HIVAN, 4 FSGS and 4 healthy controls were deparafinized and stained for ET-1. Mouse monoclonal ET-1 was used as the primary antibody and a goat anti mouse IgG conjugated to horseradish peroxidase as the secondary antibody. Samples were blinded and scored for staining intensity, 0-4 scale, in podocytes, renal tubules, the vasculature and interstitial cells.

Peripheral Blood Macrophage Culture

Peripheral blood mononuclear cells (PBMCs) from HIVAN (n=6), African American HIV$^+$ (n=7), Caucasian HIV$^+$ (n=4), healthy African American (n=4), and healthy Caucasian (n=5) controls were isolated by Histopaque density gradient separation. Macrophages were purified from the PBMC population by adherence to plastic. Briefly, PBMCs were washed in Hanks Balanced Salt Solution without Ca$^{++}$ and Mg$^{++}$ (HBSS), then resuspended in Iscoves Modified Dulbecco Medium (IMDM) with 10% male human serum. The PBMCs were plated in 6 well microtiter plates at a cell density of 1×10$^5$ cells per well and incubated at 37° C. for 24 hrs. The plates were washed twice with HBSS and the adherent cells were removed with cold trypsin-EDTA. The recovered monocytes were washed and plated in 6 well cluster plates at a density of 1×105 cells/ml in IMDM plus 10% human serum, and incubated for 5-7 days for macrophage maturation. The final cell preparations contained approximately 80% monocytes/macrophages as determined by nonspecific esterase staining. Cell viability was greater than 98%, as assessed by trypan blue exclusion.

Cells were stimulated with either 100 ng/ml LPS (*E. coli* serotype 0111:B4) as a positive control, 10 ng/ml baculovirus-derived HIV-1 gp120$_{BaL}$ (NIH AIDS Research and Reference Reagent Program), 10 ng/ml non-myristylated *E. coli*-derived recombinant HIV Nef (rHIV Nef), or media only. The rHIV Nef was tested for LPS content by the limulus amebocyte assay and found to be free of contamination. Total RNA was isolated from both resting and stimulated macrophages at 4 hours, using Tri-Reagent and frozen at −80° C.

Reverse Transcriptase-Real Time Quantitative PCR (RT qPCR)

Total RNA was reverse transcribed into cDNA using the Ominiscript® Reverse Transcriptase. The mixture was incubated for 60 mins at 37° C. One μg of RNA was converted to cDNA, of which 500 ng was used for real time qPCR. In brief, 2 μl of each primer was added to 25 μl of a 2× QuantiTect™ SYBR Green PCR master mix in RNase-free water. cDNA was added to the mixture. Real time cycler conditions were: 15 min at 95° C. (PCR initial activation step), 40 cycles of 15 s at 94° C. (denaturation), 30 s at 55° C. (annealing), and 30 s at 72° C. (extension). Specific primer sequences are listed in Table 1. Values for the amplified gene products were obtained through normalizing the gene of interest to the 18 s rRNA concentration in each sample.

Statistics

For mRNA expression and protein analysis, statistical comparisons were made using the non-parametric Mann-Whitney rank sum test for significance. For the SNP analyses, a Pearson's Chi-Square test was used to determine significant differences in the frequencies of the T alleles between groups. Results are presented as the mean±SEM. Statistical significance was defined as $P<0.05$ or less.

EXAMPLE 2: PLASMA ET-1 LEVELS IN DIFFERENT PATIENT GROUPS

As shown in FIG. 1, ET-1 in HIVAN patients was significantly elevated (4.66±0.20 μg/ml) compared to African American HIV positive (2.66±0.13 pg/ml), Caucasian HIV positive patients (1.76±0.09 pg/ml) and healthy African American (0.3±0.08 pg/ml) and Caucasian (0.44±0.12) controls ($P<0.001$ for all groups). All HIV positive patients had higher concentrations of ET-1 when compared to controls without HIV infection in the following order: HIVAN (n=65)>African American HIV$^+$ patients (n=63) ($P=<0.001$)>Caucasian HIV$^+$ patients (n=59) ($P<0.001$)> healthy African American (n=77) and Caucasian (n=58) controls ($P<0.001$). Brackets denote significant differences between groups.

EXAMPLE 3: ET-1 EXPRESSION IN KIDNEY BIOPSY SAMPLES

Figure 2:
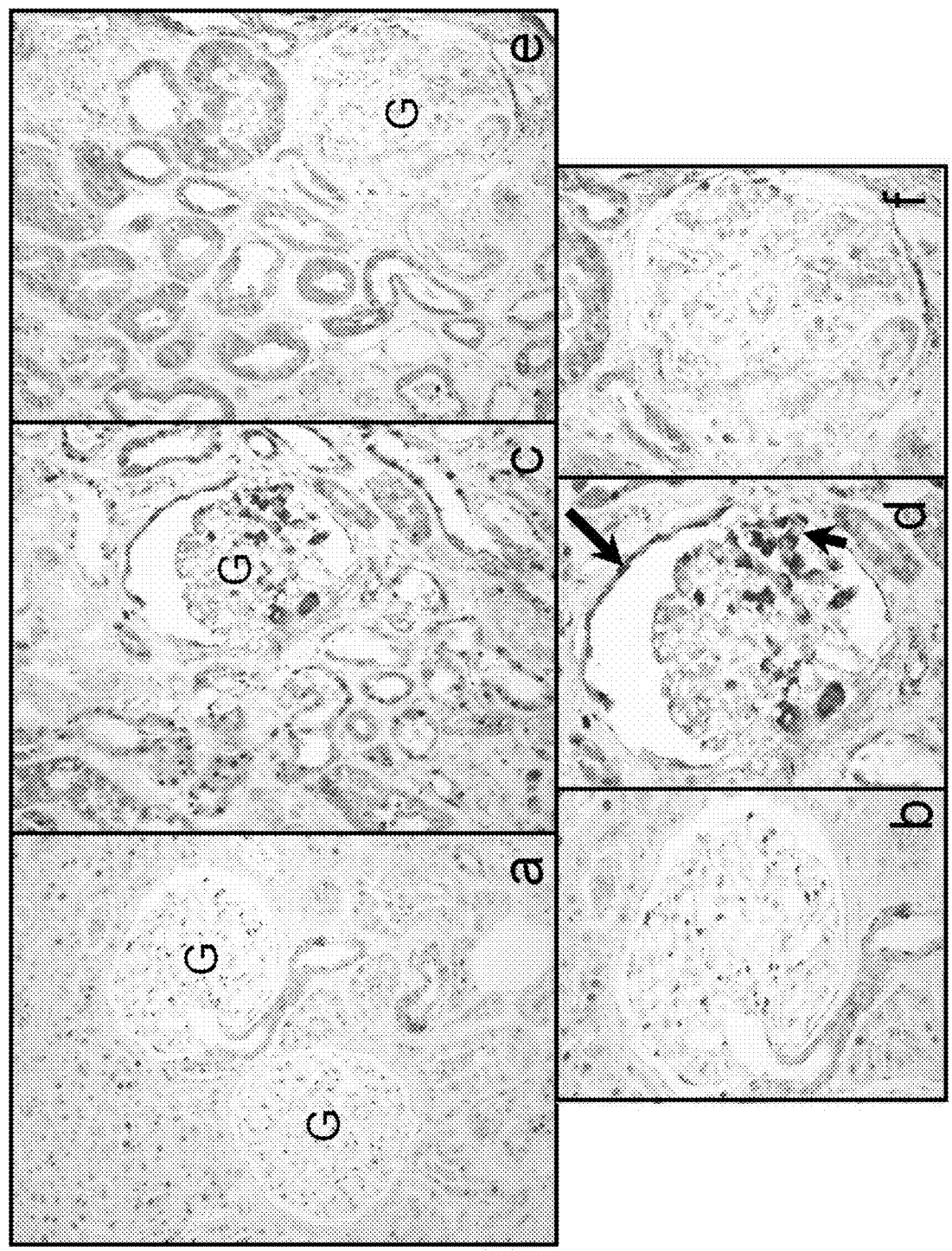
FIG. 2 is a composite of picture panels showing immunohistochemistry of ET-1 in kidney biopsies. Immunohistochemical localization of ET-1 in kidney tissue from donor nephrectomies (panels a and b) compared with renal biopsies from patients with primary (idiopathic) focal segmental glomerulosclerosis (FSGS) (panels c and d) or HIV infection (panels e and f). Original magnification of Panels a, c and e=100×. Original magnification of Panels b, d and f=200×. G=glomerulus.

As shown in FIG. 2, immunoperoxidase staining for ET-1 is negative in kidney tissue from a donor nephrectomy (panels a and b). A kidney biopsy from a patient with FSGS (panels c and d) exhibits increased content of ET-1 in parietal epithelium lining Bowman's space (large arrow in panel d), as well as visceral epithelial cells overlying a segmental scar (smaller arrow in panel d). Surrounding tubules also show increased cytoplasmic expression of ET-1. A kidney biopsy from a patient infected with HIV (panels e and f) shows increased expression of ET-1 in tubules, similar to that in the FSGS sample. In contrast to FSGS, however, glomerular epithelial cells evidence only trace amounts of the protein.

EXAMPLE 4: PPET-1 MRNA LEVELS IN DIFFERENT PATIENT GROUPS

Figure 3:
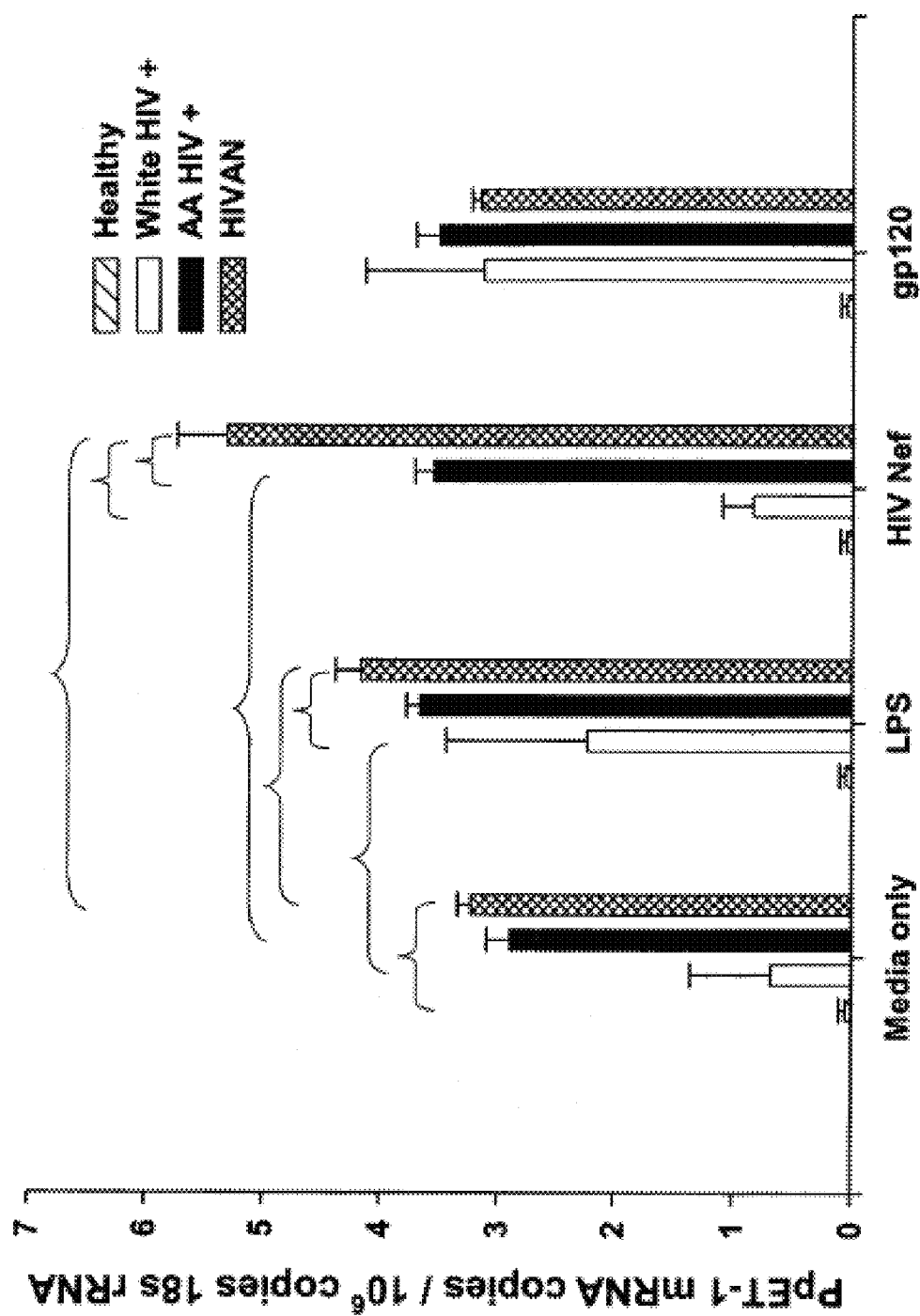
FIG. 3 is a diagram showing preproET-1 (PpET-1) mRNA expression in healthy Caucasian and African American controls (healthy, n=9), HIV positive Caucasians (White HIV+, n=4), HIV positive African Americans (AA HIV+, n=7), and HIVAN patients (n=6).

Preproendothelin-1 (ppET-1) is the precursor polypeptide processed to big ET-1 and then cleaved by ECE-1 to produce the active ET-1 peptide. Peripheral blood derived macrophage were cultured with media only (control), 100 ng/ml LPS, 10 ng/ml HIV Nef or 10 ng/ml HIV gp120 for 4 hours. PpET-1 mRNA was detected using real time quantitative PCR and normalized against 18 s rRNA. All other significant differences are denoted by the brackets. As shown in FIG. 3, all HIV positive patients had significantly higher expression of ppET-1 mRNA when compared to the healthy controls under all treatment conditions ($P<0.003$). ppET-1 mRNA expression was highest in macrophages from HIVAN patients treated with HIV Nef when compared to all other groups ($P<0.003$). African American HIV positive patients, including HIVAN patients, had significantly higher amounts of ppET-1 mRNA expressed in cells cultured in media or treated with HIV Nef compared to HIV$^+$ Caucasian patients ($P<0.003$). LPS treatment of HIVAN patients' macrophages stimulated significantly more ppET-1 ($P<0.03$) than LPS treatment of macrophages from Caucasian HIV positive patients. In all cases, except cells from the healthy controls, LPS increased ppET-1 mRNA expression when compared to cells cultured in media only ($P<0.02$).

EXAMPLE 5: ECE-1 MRNA LEVELS IN DIFFERENT PATIENT GROUPS

Figure 4:
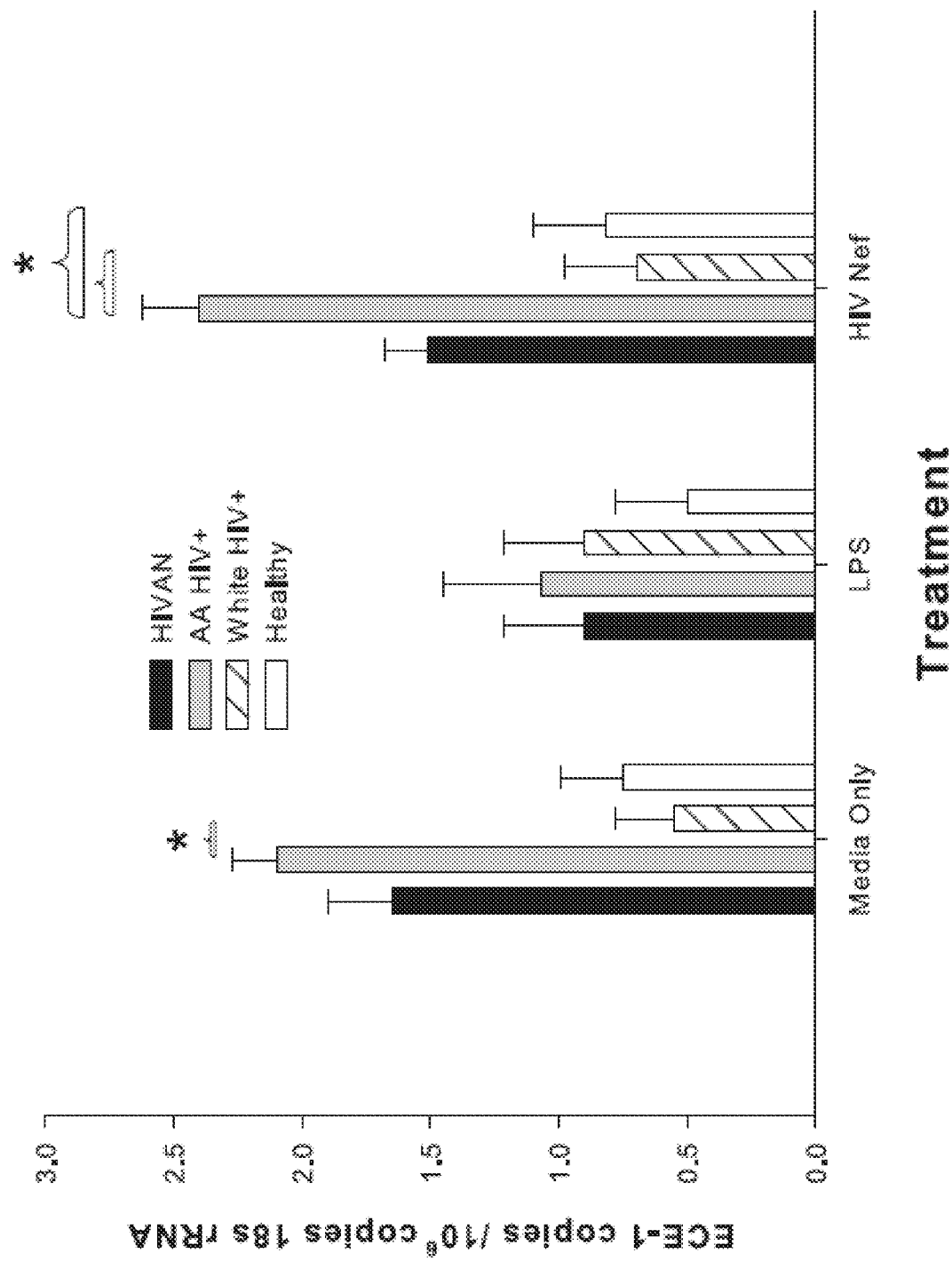
FIG. 4 is a diagram showing ECE-1 mRNA expression in healthy Caucasian and African American controls (healthy, n=9), HIV positive Caucasians (White HIV+, n=4), HIV positive African Americans (AA HIV+, n=7), and HIVAN patients (n=6).

ECE-1 converts biologically inactive big ET-1 into the biologically active ET-1 peptide. Thus, over-expression of ECE-1 can lead to increased production of ET-1. Peripheral blood derived macrophages from the above described ethnic groups were treated as described above. ECE-1 mRNA was detected using real time quantitative PCR and normalized against 18 s rRNA. Differences in macrophage ECE-1 mRNA expression between ethnic and treatment groups are shown in FIG. 4. Brackets denote significant differences between groups.

HIV Nef induced the greatest amount of ECE-1 mRNA in African American HIV positive macrophages, which was significantly higher than all the other groups ($P<0.02$). Macrophages from African American HIV positive and HIVAN patients had significantly increased ECE-1 mRNA expression when cultured in media only or treated with HIV Nef ($P<0.02$ and $P<0.001$, respectively) compared to the healthy controls and Caucasian HIV positive patients. LPS treatment did not significantly increase ECE-1 mRNA in any groups when compared to the other treatments. No significant differences were found between the Caucasian HIV positive patients responses and the healthy group. HIV gp120 did not induce any detectable ECE-1 mRNA from any of the macrophages (data not shown).

EXAMPLE 6: SNP ANALYSIS IN DIFFERENT PATIENT GROUPS

Figure 5:
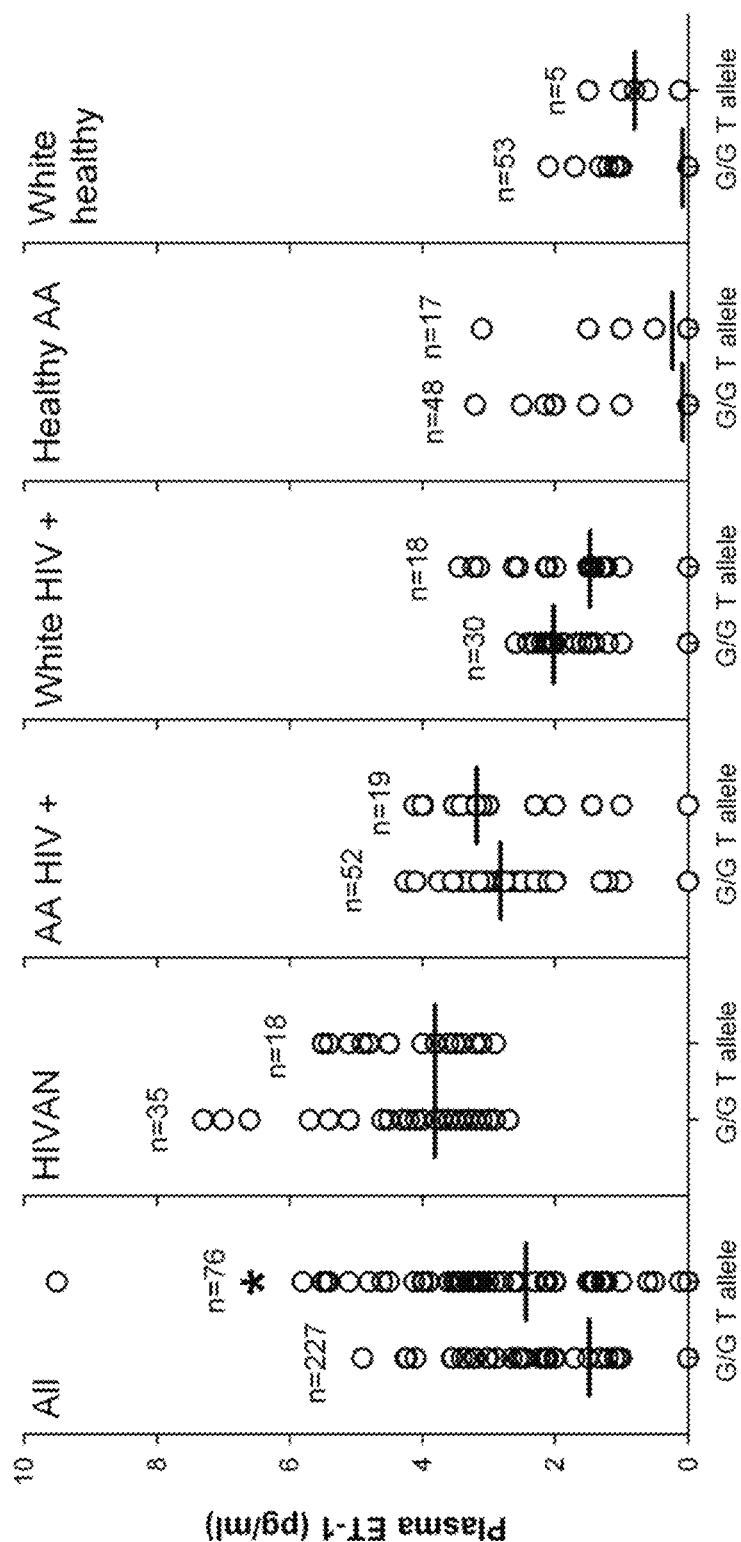
FIG. 5 is a diagram showing a SNP analysis correlating differences in plasma ET-1 expression and T allele frequencies between the following patient groups: HIVAN, AA HIV positive, non-AA HIV positive, healthy AA, and healthy non-AA.

Genomic DNA was isolated with DNAzol BD (Molecular Research Center) from PBMCs. The ET-1 SNP was amplified using Hotstart Taq PCR (Qiagen) using the specific primers listed in Table 1. Pyrosequencing (Uppsala, Sweden) was performed using the ET-1 amplified PCR products. The forward primer was biotinylated at the 5' end for use in pyrosequencing. The nucleotide sequence was determined from the signal peaks in the pyrogram. Genotypes were verified in a second laboratory using an ABI 3100 capillary nucleic acid sequencer (Applied Biosystems, Foster City, Calif.) and Taqman probes. DNA samples with discordant results were excluded from the study. The T allele frequencies between the following patient groups: HIVAN, AA HIV positive, non-AA HIV positive, healthy AA, and healthy non-AA are shown in FIG. 5.

TABLE 1

PCR Primer Sequences

| Gene | Forward Primer | Reverse Primer |
| --- | --- | --- |
| ppET-1 | TGGACATCATTTGGGTCAACTCTCTTGGACCTAGGCTTCA (SEQ ID NO: 1) | (SEQ ID NO: 2) |
| ECE-1* | AACCTTCGCCGAGGACAG (SEQ ID NO: 3) | GGCTGATTTTCGGGTTTC (SEQ ID NO: 4) |
| 18s rRNA* | GTAACCCGTTGAACCCCATTCCATCCAATCGGTAGTAGC (SEQ ID NO: 5) | G (SEQ ID NO: 6) |
| Lys198Asn | GTCGGAGACCATGAGAAACAGTTTTGAACGAGGACGCTGGCG (SEQ ID NO: 7) | GTCC (SEQ ID NO: 8) |

*Designed by Beacon Designer (Premier Biosoft International, Palo Alto, CA)

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following embodiments. The embodiments are intended to cover the components and steps in any sequence which is effective to meet the objectives there intended, unless the context specifically indicates the contrary.

What is claimed is:

1. A method for diagnosis and treatment of HIVAN in a subject, comprising:
   (a) comparing a level of ET-1 in a biological sample obtained from the subject to a threshold level of 4 pg/ml;
   (b) diagnosing the subject with HIVAN based on determining whether the subject has a plasma ET-1 level greater than the threshold, level, and based on whether the subject has an increased level of ET-1 compared to an HIV positive control subject; and
   (c) administering to the subject an ET-1 antagonist is selected from the group consisting sitaxentan, ambrisentan, atrasentan, BQ-123, bosentan and tezosentan where said subject has been diagnosed with HIVAN based on the result in step (b).

2. The method of claim 1, wherein the biological sample is blood, plasma, urine, saliva or tissue.

3. The method of claim 1, wherein ET-1 antagonist is administered by a local infusion into a kidney of the subject.

4. The method of claim 1, wherein the ET-1 antagonist is administered by a local infusion into a kidney of the subject.

5. The method of claim 1, wherein the subject does not have diabetes.

6. The method of claim 1, wherein the subject is further administered an ACE inhibitor.

7. The method of claim 1, wherein the subject is administered a composition consisting of two active agents, an ET-1 antagonist and an angiotensin-converting enzyme (ACE) inhibitor.

8. The method of claim 1, wherein the ACE inhibitor is selected from the group consisting of enalapril, ramipril, quinapril, perindopril, lisinopril, benazepril, imidapril, and zofenopril.

9. The method of claim 1, wherein the ET-1 antagonist is administered by a close-circuit perfusion into a kidney of the subject.

10. The method of claim 1, wherein the close-circuit perfusion is performed for a range of 10-60 minutes.

11. The method of claim 9, wherein the ET-1 antagonist is infused through a retrograde catheter into the pyelic cavity.

* * * * *

UNITED STATES PATENT AND TRADEMARK OFFICE
CERTIFICATE OF CORRECTION

PATENT NO. : 11,372,005 B2
APPLICATION NO. : 17/094175
DATED : June 28, 2022
INVENTOR(S) : Gale W. Newman, James W. Lillard, Jr. and Chamberlain Obialo Page 1 of 1

It is certified that error appears in the above-identified patent and that said Letters Patent is hereby corrected as shown below:

In the Specification

At Column 1, Lines 13-16, currently reads:
"This application was made with U.S. Government support under Grant No. 5P20RR011104, awarded by the NIH/NCDD/Clinical Research Centers. Thus, the U.S. Government may have certain rights in this application."

Should Read:
"This invention was made with government support under 5P20RR011104 awarded by The National Institute of Health. The government has certain rights in the invention."

Signed and Sealed this
First Day of July, 2025

Coke Morgan Stewart
*Acting Director of the United States Patent and Trademark Office*